United States Patent [19]

Heilmann et al.

[11] Patent Number: 4,931,582

[45] Date of Patent: Jun. 5, 1990

[54] FLUORINATED, ACRYLAMIDE-FUNCTIONAL MONOMERS

[75] Inventors: Steven M. Heilmann; Larry R. Krepski; Dean M. Moren; Jerald K. Rasmussen; Howell K. Smith, II, all of St. Paul, Minn.

[73] Assignee: Minnesota Mining and Manufacturing Company, St. Paul, Minn.

[21] Appl. No.: 267,186

[22] Filed: Nov. 4, 1988

[51] Int. Cl.$^5$ .................................... C07C 103/48
[52] U.S. Cl. ...................... 560/172; 560/41; 560/122; 560/123; 560/124; 560/125
[58] Field of Search ............. 560/172, 41, 122, 123, 560/124, 125

[56] References Cited

U.S. PATENT DOCUMENTS

| | | | |
|---|---|---|---|
| 2,743,297 | 4/1956 | Husted et al. | 260/561 |
| 2,957,914 | 10/1960 | Halpern et al. | 260/561 |
| 3,475,434 | 10/1969 | Knell | 260/268 |
| 3,655,732 | 4/1972 | Rondestvedt | 260/486 |
| 3,997,604 | 12/1976 | Foulletier et al. | 260/561 |
| 4,021,224 | 5/1977 | Pallos et al. | 560/172 |
| 4,447,493 | 5/1984 | Driscoll et al. | 428/332 |

OTHER PUBLICATIONS

"Polyazlactones", Encyclopedia of Polymer Science and Engineering, vol. 11, 2nd Ed., 1988.
L. D. Taylor, et al., J. Polymer Sci. Polymer Lett., 7, 597 (1969).

Primary Examiner—Bruce Gray
Attorney, Agent, or Firm—Donald M. Sell; Walter N. Kirn; Lorraine R. Sherman

[57] ABSTRACT

Novel fluorinated, acrylamide monomers are prepared from 2-alkenyl azlactones reacted with fluorinated alcohols. The novel monomers have the formula

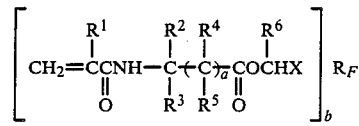

wherein
$R^1$ and $R^6$ are independently hydrogen or methyl;
$R^2$ and $R^3$ independently can be an alkyl, cycloalkyl, or aryl group, or $R^2$ and $R^3$ taken together with the carbon to which they are joined can form a carbocyclic ring containing 4 to 12 ring atoms;
$R^4$ and $R^5$ are independently hydrogen or lower alkyl;
a is 0 or 1;
b is 1 or 2;
X is a single bond, $CH_2$, $CH_2OCH_2$, and $CH_2CH_2OCH_2$; and
$R_F$ is a substantially perfluorinated alkyl, cycloalkyl, or aryl group when b is 1 and perfluorinated alkylene when b is 2.

Novel polymers and copolymers can be prepared from the monomers of the invention.

5 Claims, No Drawings

FLUORINATED, ACRYLAMIDE-FUNCTIONAL MONOMERS

FIELD OF THE INVENTION

This invention relates to novel fluorinated, acrylamide-functional monomers and a process therefor. In another aspect, this invention provides homo- and copolymers of the fluorinated, acrylamide-functional monomers. Polymers derived from the novel acrylamide monomers of the invention find utility, for example, in stain resistant coatings.

BACKGROUND OF THE INVENTION

Substitution of fluorine for hydrogen in polymers and coatings is often desirable to impart useful properties such as lower surface energy which is necessary for stain resistance. Typically, the incorporation of fluorine into polymers and coatings has been made by copolymerizing (meth)acrylate monomers derived from (meth)acrylic acid and highly fluorinated alcohols. These fluorinated (meth)acrylate monomers are available commercially from several sources. Despite their general availability, however, (meth)acrylates often polymerize at slow rates and provide polymers which possess inadequate thermal and hydrolytic stabilities.

Fluorinated (meth)acrylamide monomers have been described in several patents. U.S. Pat. Nos. 2,743,297; 2,957,914; and 3,997,604 disclose fluorinated (meth)acrylamide monomers prepared by the reaction of fluorinated secondary or primary amines and (meth)acryloyl chloride; a complication in the synthesis is removal of the hydrogen chloride by-product. U.S. Pat. No. 3,475,434 teaches the reaction of a stoichiometric excess (about 300 percent) of a short chain diamine with a perfluorinated acylating agent, isolation and purification of the monoperfluoroamide, and (meth)acryloylation of the remaining amine function with the appropriate acid chloride; here again hydrogen chloride is a troublesome by-product, and the complexity of the synthesis is self-evident. U.S. Pat. No. 3,655,732 teaches a multi-step synthesis of fluorinated acrylamides which possess a heteroatom, typically sulfur, as part of a five atom linking group between the acrylamide and perfluorinated moieties.

2-Alkenyl azlactones are known to react with certain nucleophiles such as primary amines and alcohols to afford (meth)acrylamide-functional products. The interested reader is referred to our recent review article entitled "Polyazlactones" which is contained in the *Encyclopedia of Polymer Science and Engineering*, Volume 11, 2nd edition, 1988. The reaction product of 2-vinyl-4,4-dimethylazlactone and 2,2,2-trifluoroethylamine is a high melting solid (m.p. 135°–136° C.), having been reported by L. D. Taylor, et al., *J. Polymer Sci. Polymer Lett.*, 7, 597 (1969). U.S. Pat. No. 4,447,493 discloses the reaction product of a 2-alkenyl azlactone and poly(perfluorooxyalkylene) polyols, but these materials contain main chain heteroatoms (oxygen) and often yield highly colored reaction products which can be undesirable; additionally, the highly oxygenated, relatively high molecular weight reaction products tend to be less compatible with other necessary additives such as monomers, crosslinking agents, and photoinitiators.

SUMMARY OF THE INVENTION

Briefly, the present invention provides novel fluorinated acrylamide monomers and homo- and copolymers prepared therefrom.

The fluorinated acrylamide monomers are prepared by the reaction of 2-alkenyl azlactones and fluorinated alcohols. The reaction is facilitated by the lack of formation of any product other than the fluorinated acrylamide monomer and is therefore extremely efficacious from a synthesis viewpoint. As expected, the novel acrylamide monomers polymerize at high rates, and the resulting polymers are environmentally quite stable. An unexpected and significant benefit observed with the instant polymers is improved toughness.

In this application:

"acrylamide" and "acrylate" mean both so-called acryloyl, i.e., 2-propenoyl, and methacryloyl, i.e., 2-methyl-2-propenoyl, amine and alcohol derivatives;

"substantially perfluorinated" means hydrocarbon groups in which at least 50 percent of the hydrogen atoms have been replaced by fluorine;

"alkyl" and "alkylene" mean the monovalent and divalent residues remaining after removal of one and two hydrogen atoms, respectively, from a linear or branched chain hydrocarbon having 1 to 20 carbon atoms;

"lower alkyl" means $C_1$ to $C_4$ alkyl;

"aryl" means the monovalent residue remaining after removal of a hydrogen atom from an aromatic compound (single ring and multi- and fused-ring) having 5 to 12 ring atoms and includes substituted aromatics such as lower alkaryl and aralkyl, lower $C_1$ to $C_4$ alkoxy, N,N-di(lower alkyl)amino, nitro, cyano, halo, and lower alkyl carboxylic ester, wherein "lower" means $C_1$ to $C_4$;

"azlactone" means 2-oxazolin-5-one groups of Formula I and 2-oxazin-6-one groups of Formula II:

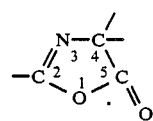

I

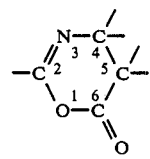

II

"cycloalkyl" means the monovalent residue remaining after removal of a hydrogen atom from a cyclic hydrocarbon having 3 to 12 carbon atoms;

The monomers of the present invention exhibit high rates of free radical homo- and copolymerization and yield toughened polymers compared to those resulting from acrylate- or methacrylate-functional monomers.

A significant advantage of using the 2-alkenyl azlactone as an acylating agent in the present invention method instead of acryloyl chloride as in the prior art method is that the azlactone/nucleophile reaction involves ring-opening addition; no smaller by-product molecule (such as hydrogen chloride) is displaced or generated in the reaction.

The acrylamide functionality can offer certain advantages as a polymerizable group over the acrylate. The amide group is known to be more difficult to hydrolyze than the ester group, and amide-functional polymers should therefore be more environmentally stable. Additionally, according to information published in the *Polymer Handbook*, 2nd edition, edited by J. Brandrup and E. H. Immergut, Wiley-Interscience, New York, 1975, pp. II 47–49, acrylamides enjoy rates of free radical polymerization substantially faster than corresponding acrylates or methacrylates. N,N-Dimethylacrylamide, for example, exhibits a rate of bulk polymerization ($k_p^2/k_t$) at 50° C. 1142 times faster than methyl acrylate and 457 times faster than methyl methacrylate. Despite these potential advantages, however, there are presently no fluorinated acrylamide monomers that are commercially available.

DETAILED DESCRIPTION OF THE INVENTION

The present invention provides a new class of fluorinated, acrylamide monomers having the general Formula III:

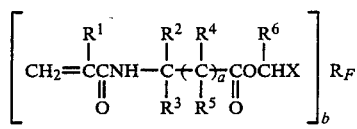

wherein
$R^1$ and $R^6$ are independently hydrogen or methyl;
$R^2$ and $R^3$ independently can be an alkyl, cycloalkyl, or aryl group, or $R^2$ and $R^3$ taken together with the carbon to which they are joined can form a carbocyclic ring containing 4 to 12 ring atoms;
$R^4$ and $R^5$ are independently hydrogen or lower alkyl;
a is 0 or 1;
b is 1 or 2;
X is a single bond, $CH_2$, $CH_2OCH_2$, and $CH_2CH_2OCH_2$; and
$R_F$ is a substantially perfluorinated alkyl, cycloalkyl, or aryl group when b is 1 and perfluorinated alkylene when b is 2.

The novel fluorinated, acrylamide monomers of Formula III are prepared by reaction of 2-alkenyl azlactones having the general Formula IV

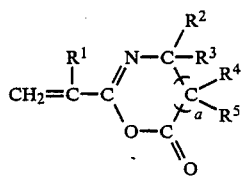

(wherein $R^1$, $R^2$, $R^3$, $R^4$, $R^5$ and a are as previously defined) with a fluorinated alcohol having the general Formula V:

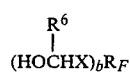

(wherein b, X, $R^6$, and $R_F$ are as previously defined)

2-Alkenyl azlactones are well-known and their synthesis, physical and chemical properties, homo- and copolymerization behavior, and applications are discussed in our recent review entitled "Polyazlactones" previously cited. Useful 2-alkenyl azlactones for the present invention include 2-vinyl-4,4-dimethyl-2-oxazolin-5-one, 2-isopropenyl-4,4-dimethyl-2-oxazolin-5-one, 2-vinyl-4-ethyl-4-methyl-2-oxazolin-5-one, 2-vinyl-4,4-diethyl-2-oxazolin-5-one, 2-vinyl-4-methyl-4-phenyl-2-oxazolin-5-one, 2-isopropenyl-4,4-tetramethylene-2-oxazolin-5-one, 2-vinyl-4,4-pentamethylene-2-oxazolin-5-one, and 2-vinyl-4,4-dimethyl-2-oxazin-6-one.

The preferred 2-alkenyl azlactone because of its reactivity and commercial availability is 2-vinyl-4,4-dimethyl-2-oxazolin-5-one (SNPE, Paris, France). In certain applications that employ radiation curing or photopolymerization situations in which no solvent is present, however, it is extremely desirable that the fluorinated, acrylamide monomer be a liquid at room temperature or slightly above. In those instances the melting point of the fluorinated, acrylamide monomer product can be lowered (relative to $R^1$=H; $R^2$=$R^3$=methyl; and a =0) by utilizing an alkenyl azlactone which contains an asymmetric carbon atom at position-4 or a six-membered azlactone compound. In those instances, 2-vinyl-4-ethyl-4-methyl-2-oxazolin-5-one and 2-vinyl-4,4-dimethyl-2-oxazin-6-one are preferred, and references for their synthesis are given in our "Polyazlactones" review, supra.

Useful fluorinated alcohols of the present invention which are commercially available include 1H,1H,7H-dodecafluoro-1-heptanol, perfluorocyclohexyl-1H,1H-methanol, 2,2,3,3,4,4,5,5,6,6-decafluoro-1-methylheptanol-1, 1H,1H,11H-eicosafluoro-1-undecanol, 1H,1H-heptafluoro-1-butanol, 1H,1H,9H-hexadecafluoro-1-nonanol, hexafluoroisopropanol, 1H,1H,5H-octafluoro-1-pentanol, 1H,1H-pentadecafluorooctanol, pentafluorobenzyl alcohol, 1H,1H-pentafluoropropanol, 1H,1H,2H,2H-perfluorodecanol-1, 1H,1H,2H,2H-perfluorododecanol-1, 1H,1H,3H-tetrafluoro-1-propanol, 2,2,2-trifluoroethanol, 2,2,3,3-tetrafluoro-1,4-butanediol, 2,2,3,3,4,4-hexafluoro-1,5-pentanediol, and 2,2,3,3,4,4,5,5-octafluoro-1,6-hexanediol.

Other fluorinated alcohols useful in the invention, especially when low melting acrylamide reaction products are desired, are those described in our copending patent application entitled "O-Hydroxyalkylation of 1,1-Dihydroperfluorinated Alcohols", U.S. Pat. No. 4,906,792, filed the same date as this application, which is incorporated herein by reference.

The reaction of the 2-alkenyl azlactone and the fluorinated alcohol is facilitated by the presence of a catalyst. Useful catalysts include 1,8-diazabicyclo[5.4.0]undec-7-ene (DBU), 1,5-diazabicyclo[4.3.0]non-5-ene (DBN), triethylamine, 1,4-diazabicyclo[2.2.2]octane (DABCO), trioctylphosphine, and tributylphosphine in molar concentrations of from 0.1 to 20 weight percent, preferably 0.25–5.0 weight percent, and most preferably 0.5–2.0 weight percent based on the azlactone reactant; DBU, DBN, and trioctylphosphine are preferred. In a typical procedure, equal molar quantities of 2-alkenyl azlactone and fluorinated alcohol are mixed with the catalyst in the absence of solvent. Alternatively, solvents may be employed with the provision that they not react with the azlactone or catalyst under the reaction conditions. Suitable organic solvents include ethyl acetate, toluene, tetrahydrofuran, and fluorinated solvents such as Freon TM 113 (Du Pont). Especially with the preferred catalysts and a solvent-free reaction solution, a mildly exothermic reaction will ensue, and the reaction is generally complete as determined by infrared spectroscopy when the reaction temperature returns to ambient. At this point the fluorinated, acrylamide monomer product is either a crystalline solid or a viscous liquid, and for most purposes further purification is unnecessary.

With other catalysts and when solvents are employed, warming the reaction mixture will hasten completion of reaction. It is generally advisable to add a free radical stabilizer such as phenothiazine or 2,6-di-t-butyl-p-cresol in concentrations by weight based on reaction product of from 0.01 to 1.0 percent, preferably 0.05–0.15 percent. Suitable warming conditions are from 40°–80° C., preferably 40°–65° C. for a period of 0.5–12 hours, preferably 0.5–2 hours.

As is apparent to one skilled in the art, the fluorinated, acrylamide monomers of the invention can be polymerized by standard thermally- or photochemically-initiated free radical addition polymerization procedures. Also apparent is that copolymers can be prepared from the instant monomers and essentially any free radically polymerizable olefin by employing standard techniques. The polymerizations can be effected in the absence of solvents, if the monomer formulations are liquid at the polymerization temperatures, or in solution, and several useful, non-reactive solvents have been specified above. Polymers and copolymers can have molecular weights in the range of approximately 20,000 to 5,000,000.

Polymers and copolymers of the invention contain structural units of Formula VI (when b=1) or VII (when b=2), respectively, which are as follows:

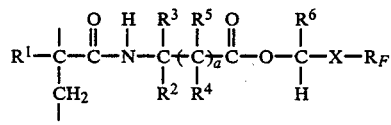

VI and

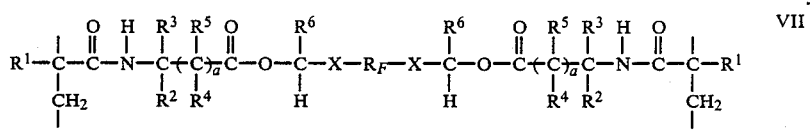

VII wherein $R^1$, $R^2$, $R^3$, $R^4$, $R^5$, $R^6$, $R_F$, a, X are as previously defined and the open dashes (—) mean an attachment to a polymer main-chain.

An excellent discussion of suitable olefinic monomers for use in preparing copolymers of the invention is contained in C. E. Schildknecht's text "Vinyl and Related Polymers", Wiley, N.Y., 1959. Examples include: the Vinyl aromatic monomers such as styrene, α-methylstyrene, and 2-and 4-vinylpyridine; α,β-unsaturated carboxylic acids such as acrylic acid, methacrylic acid, itaconic acid, maleic acid, fumaric acid, and crotonic acid; α,β-unsaturated carboxylic acid derivatives such as methyl methacrylate, butyl methacrylate, 2-ethylhexyl methacrylate, ethyl acrylate, butyl acrylate, isooctyl acrylate, octadecyl acrylate, cyclohexyl acrylate, tetrahydrofurfuryl acrylate, phenyl acrylate, phenethyl acrylate, benzyl acrylate, cyanoethyl acrylate, diethyl itaconate, acrylamide, acrylonitrile, N,N-dimethylacrylamide, and N-butylacrylamide; vinyl esters of carboxylic acids such as vinyl acetate, and vinyl 2-ethylhexanoate; vinyl halides such as vinyl chloride and vinylidene chloride; vinyl ethers such as methyl vinyl ether, 2-ethylhexyl vinyl ether, and butyl vinyl ether; olefins such as ethylene; N-vinyl compounds such as N-vinylpyrrolidone and N-vinylcarbazole; vinyl ketones such as methyl vinyl ketone; and vinyl aldehydes such as acrolein and methacrolein. The preferred monomers for the purposes of the present invention are the α,β-unsaturated carboxylic acid derivatives.

A surprising feature of the polymers prepared from the fluorinated, acrylamide monomers of the invention is their superior toughness (i.e., at least 25 percent greater) relative to corresponding acrylate polymers which contain the same fluorinated group. This is especially surprising in light of previous work (S. M. Heilmann and H. K. Smith II, J. Appl. Polymer Sci., 24, 1551 (1979)) conducted on pressure sensitive adhesives. In that work it was well established that a secondary amide group (—CONH—) immediately pendant from a polymer main-chain was sterically incapable of participating in hydrogen bonding between polymer chains (necessary for building cohesion). This was so primarily because of the group's immediate proximity to the very large and bulky polymer main-chain. Yet in the present invention, as is exemplified below, the same immediately pendant secondary amide groups somehow cause a substantial toughening to occur. While not wishing to be bound by any explanation and yet to explain our invention as fully as possible, it is felt that the toughening effect can be attributed to increased double bond character of the carbon-nitrogen amide bond. The secondary amide bond functions as a rigid, orientating side group relative to the carbon-oxygen ester bond in acrylates and, in this fashion, is better able to absorb and dissipate mechanical stress, thereby exerting a toughening influence.

The fluorinated, acrylamide monomers of the invention intrinsically possess low surface energies, as do the polymers and copolymers produced from them. The monomers find use as components in stain resistant coatings for surfaces. One such application as a stain resistant coating for fabric is exemplified below.

Objects and advantages of this invention are further illustrated by the following examples, but the particular materials and amounts thereof recited in these examples, as well as other conditions and details, should not be construed to unduly limit this invention.

EXAMPLE 1

Preparation of 1H,1H,2H,2H-Perfluorodecyl 2-Acrylamido-2-methylpropionate 1H,1H,2H,2H-Perfluoro-1-decanol (available from Strem Chemicals, Inc., Newburyport, Mass.) (13.28 grams, 0.028 mole) and 2-vinyl-4,4-dimethylazlactone (VDM) (available from SNPE, Inc., Princeton, N.J.)

(3.98 grams, 0.028 mole) were mixed and warmed to melt the fluorinated alcohol and facilitate dissolution. To this solution cooled to room temperature was added 1,8-diazabicyclo[5.4.0]undec-7-ene (DBU) (available from Aldrich Chemical Co., Milwaukee, Wis.) (0.08 gram, 0.00056 mole) which caused a warming of the reaction solution to about 40° C. When the reaction solution had cooled to room temperature, an infrared spectrum showed characteristic absorptions for the acrylamide product: 3.05 (NH stretch), 5.75 (ester C=O), 6.05 (amide C=O), 6.15 (C=C), and 6.50 (amide II) microns. Upon standing overnight, the reaction product crystallized and melted at 30°–35° C.

EXAMPLES 2–23

Employing the procedure of EXAMPLE 1, several fluorinated acrylamide monomers of Formula III which possess the specific structures indicated in Table 1 were prepared.

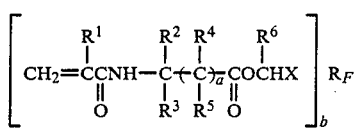

acrylate (Monomer-Polymer & Dajac, Trevose, Pa.) (viscosity about 1 cps) and the Darocur were irradiated in bulk in a Pyrex ® vessel with Blacklight to obtain a thickened coatable syrup (viscosity about 1500 cps). This syrup was then coated at 1.9 mm (75 mils) and polymerized as described above. The stress-strain relationships of 1.27 cm (0.5 inch) wide samples of the two non-tacky, conformable polymer films were recorded using a Universal Test Machine (available from Instron Corp., Canton, Mass.; crosshead rate: 2 cm/min). The poly(fluorinated, acrylamide monomer) exhibited a toughness (at yield) of 3313 cm-g/mL (47 in-lbs/in³), while the poly(1,1-dihydroperfluorooctyl acrylate) gave a toughness value of 2115 cm-g/mL (30 in-lbs/in³).

EXAMPLE 25

This example teaches the use of a fluorinated, acrylamide monomer of the invention in a stain resistant preparation for fabrics.

| Preparation of the Stain Resistant Polymer | |
|---|---|
| Charge: | |
| 1H,1H,2H,2H-perfluorodecyl 2-acrylamido-2-methylpropionate (Example 1) | 13.89 grams |

TABLE I

| Example | $R^1$ | $R^2$ | $R^3$ | a | $R^4$ | $R^5$ | $R^6$ | X | b | $R_F$ | m.p. (°C.)* |
|---|---|---|---|---|---|---|---|---|---|---|---|
| 2 | H | Me$^f$ | Me | 0 | — | — | H | sb$^d$ | 1 | $CF_3(CF_2)_2$ | 45 |
| 3 | Me | Ph$^g$ | Ph | 0 | — | — | H | sb | 1 | $CF_3(CF_2)_2$ | 79 |
| 4 | H | Me | Me | 0 | — | — | H | sb | 1 | $H(CF_2)_4$ | 48 |
| 5 | H | Me | Me | 0 | — | — | H | sb | 1 | $H(CF_2)_6$ | 52 |
| 6$^e$ | H | Me | Me | 0 | — | — | H | sb | 1 | $CF_3(CF_2)_6$ | 53 |
| 7 | H | Me | Me | 0 | — | — | Me | $CH_2OCH_2$ | 1 | $CF_3(CF_2)_6$ | <22 |
| 8 | H | Me | Me | 0 | — | — | H | sb | 1 | $c\text{-}C_6F_{11}$ | 99 |
| 9 | H | Me | Me | 0 | — | — | H | $CH_2$ | 1 | $NSO_2(CF_2)_7CF_3$ Et | 103 |
| 10 | H | Me | Et$^h$ | 0 | — | — | H | sb | 1 | $CF_3(CF_2)_6$ | <22 |
| 11 | H | Me | Me | 1 | H | H | H | sb | 1 | $CF_3(CF_2)_6$ | <22 |
| 12 | H | Me | Me | 0 | — | — | H | $CH_2OCH_2$ | 1 | $CF_3(CF_2)_6$ | <22 |
| 13 | Me | Me | Me | 0 | — | — | H | sb | 1 | $CF_3(CF_2)_6$ | 72 |
| 14 | H | Me | Me | 0 | — | — | H | sb | 2 | $(CF_2)_4$ | 145 |
| 15 | H | Me | Et | 0 | — | — | H | sb | 2 | $(CF_2)_4$ | 146 |
| 16 | H | Me | Et | 0 | — | — | H | sb | 2 | $(CF_2)_3$ | 95 |
| 17 | H | Me | Et | 0 | — | — | H | sb | 2 | $(CF_2)_2$ | 151 |
| 18 | H | Me | Et | 0 | — | — | H | $CH_2$ | 1 | $CF_3(CF_2)_7$ | <22 |
| 19 | H | Me | Me | 1 | H | H | H | $CH_2$ | 1 | $CF_3(CF_2)_7$ | 25 |
| 20 | H | Me | Me | 0 | — | — | H | sb | 2 | $(CF_2)_2$ | 105 |
| 21 | H | Me | Me | 1 | H | H | H | sb | 2 | $(CF_2)_3$ | <22 |
| 22 | H | Me | Me | 1 | H | H | H | sb | 1 | $H(CF_2)_6$ | <22 |
| 23 | H | Me | Et | 0 | — | — | H | sb | 1 | $H(CF_2)_6$ | <22 |

*Melt temperatures were measured on unrecrystallized samples. The upper temperature of the melting range is recorded at which a clear melt is present.
$^d$sb means single bond
$^e$This Example was conducted using trioctylphosphine (2 mol %) instead of DBU as catalyst.
$^f$Me = Methyl
$^g$Ph = phenyl
$^h$Et = ethyl

EXAMPLE 24

This example illustrates the improved toughness observed in polymers prepared with the novel fluorinated, acrylamide monomers of the invention compared to corresponding poly(acrylates).

The fluorinated, acrylamide monomer of Example 6 containing 0.5 weight percent of a photoinitiator (Darocur ™ 1116, Merck, Darmstadt, West Germany) was coated onto a silicone treated paper backing at a thickness of 1.9 mm (75 mils). The coating was exposed to a lamp emitting radiation with wavelengths between 300 and 400 nm (Blacklight ™, Sylvania) in a nitrogen atmosphere for 30 minutes. 1,1-Dihydroperfluorooctyl

| n-butyl acrylate | 7.48 grams |
|---|---|
| 1,1,1-trichloroethane | 49.86 grams |
| azobis(iso-butyronitrile) | 0.11 grams |

The charge solution was degassed briefly with nitrogen in a four ounce bottle. The bottle was sealed and heated with agitation at 55° C. for 22 hours. At that point the copolymer solution was clear and very viscous; the copolymer weight percent solids was 29.2 percent, indicating greater than 97 percent conversion of monomers to copolymer.

Evaluation of the Stain Resistance of the Copolymer

A portion of the above copolymer solution was diluted with additional 1,1,1-trichloroethane to 0.7 percent solids. The stain resistant properties of the instant copolymer were compared both to untreated fabrics and fabrics treated in analogous fashion with 3M's SCOTCHGARD fabric protector. The evaluation procedure was that reported by C. L. Steel, *Book Pap. - Int. Conf. Exhib., AATCC*, 237-247 (1986). The fabrics evaluated and results obtained are shown in TABLE II below:

TABLE II

| Fabric Number | Description |
|---|---|
| 1 | rayon face velvet - lt. green |
| 2 | nylon flat upholstery - ready for printing, scoured and rubberized |
| 3 | 100% cotton woven print |
| 4 | nylon taffeta, lt. wt. single ply, uncoated |
| 5 | 12 oz. wool woven worsted gabardine, off-white |
| 6 | cotton sheeting - white, bleached, and mercerized |

| Fabric | Oil$^e$ | Water$^f$ | Spray$^g$ | Abrasion$^h$ | Soil$^i$ |
|---|---|---|---|---|---|
| UNTREATED RESULTS: | | | | | |
| 1 | 0 | 0 | 0 | 0 | 3 |
| 2 | 0 | 0 | 0 | 0 | 2 |
| 3 | 0 | 0 | 0 | 0 | 3 |
| 4 | 0 | 0 | 0 | 0 | 3 |
| 5 | 0 | 1 | 70 | 0 | 2 |
| 6 | 0 | 0 | 0 | 0 | 2.5 |
| EXAMPLE 25 RESULTS: | | | | | |
| 1 | 5 | 6 | 70 | 2 | 3 |
| 2 | 4 | 6 | 70 | 3 | 1.5 |
| 3 | 3 | 4 | 80 | 2 | 2.5 |
| 4 | 3 | 5 | 70 | 2 | 2.5 |
| 5 | 6 | 6 | 100 | 2 | 2.5 |
| 6 | 2 | 5 | 80 | 2 | 1.5 |
| SCOTCHGARD RESULTS: | | | | | |
| 1 | 5 | 7 | 70 | 2 | 3.5 |
| 2 | 5 | 5 | 80 | 5 | 2.5 |
| 3 | 6 | 8 | 80 | 5 | 4 |
| 4 | 4 | 5 | 70 | 3 | 3 |
| 5 | 6 | 8 | 100 | 3 | 2.5 |
| 6 | 5 | 4 | 70 | 4 | 3 |

$^e$oil repellency; scale 0-8; 8 = best
$^f$water/alcohol resistance; scale F-10; 10 = best
$^g$spray rating; scale 0-100; 100 = best
$^h$abrasion resistance scale 0-8; 8 = best
$^i$soil resistance; scale 0-5; 5 = best The above results with the various fabrics and stain preparations indicate that the copolymer of Example 25 is far superior to no treatment and compares favorably with a commercial fabric protection product.

Various modifications and alterations of this invention will become apparent to those skilled in the art without departing from the scope and spirit of this invention, and it should be understood that this invention is not to be unduly limited to the illustrative embodiments set forth herein.

We claim:

1. A compound having the formula

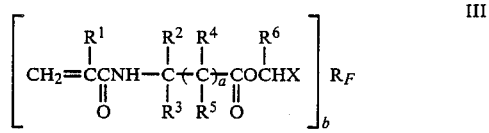

III wherein
$R^1$ and $R^6$ are independently hydrogen or methyl;
$R^2$ and $R^3$ independently are alkyl, cycloalkyl, or aryl group, or $R^2$ and $R^3$ taken together with the carbon to which they are joined form a carbocyclic ring containing 4 to 12 ring atoms;
$R^4$ and $R^5$ are independently hydrogen or lower alkyl;
a is 0 or 1;
b is 1 or 2;
X is a single bond, $CH_2$, $CH_2OCH_2$, or $CH_2CH_2OCH_2$; and
$R_F$ is an alkyl, cycloalkyl, or aryl group when b is 1 and alkylene when b is 2, wherein at least 50 percent of the hydrogen atoms have been replaced by fluorine.

2. The compound according to claim 1 wherein $R^1$ is hydrogen.

3. The compound according to claim 1 wherein $R^2$ and $R^3$ are independently lower alkyl of $C_1$ to $C_4$.

4. The compound according to claim 1 wherein $R^6$ is hydrogen.

5. The compound according to claim 1 wherein a is 1 and $R^4$ and $R^5$ are hydrogen.

* * * * *